United States Patent [19]
Mougin

[11] Patent Number: 6,159,457
[45] Date of Patent: Dec. 12, 2000

[54] COSMETIC OR DERMATOLOGICAL COMPOSITIONS CONTAINING POLYMERS EXHIBITING A CRITICAL TEMPERATURE OF THE LCST TYPE OR OF THE USCT TYPE OF USES THEREOF

[75] Inventor: Nathalie Mougin, Paris, France

[73] Assignee: L'Oreal, Paris, France

[21] Appl. No.: 09/021,124

[22] Filed: Feb. 10, 1998

[30] Foreign Application Priority Data

Feb. 10, 1997 [FR] France ................................ 97 01499

[51] Int. Cl.⁷ .............................. A61K 7/48; A61K 7/02; A61K 7/06; A61K 7/043; A61K 7/047
[52] U.S. Cl. ........................ 424/78.03; 424/47; 424/61; 424/69; 424/70.1; 424/70.13; 424/70.14; 424/70.16; 424/70.17; 424/70.19
[58] Field of Search .......................... 424/61, 401, 70.1, 424/70.13, 70.14, 70.16, 70.17, 78.03, 70.19, 69, 47

[56] References Cited

U.S. PATENT DOCUMENTS

| | | | |
|---|---|---|---|
| 3,927,199 | 12/1975 | Micchelli et al. | 424/47 |
| 4,867,966 | 9/1989 | Grollier et al. | |
| 5,019,377 | 5/1991 | Torgerson | 424/70.17 |
| 5,147,923 | 9/1992 | Mueller | 524/555 |
| 5,484,610 | 1/1996 | Bae | 424/487 |
| 5,587,404 | 12/1996 | Kroner et al. | 522/85 |
| 5,707,635 | 1/1998 | Deckner et al. | 424/401 |

FOREIGN PATENT DOCUMENTS

| | | |
|---|---|---|
| 0455081 | 11/1991 | European Pat. Off. |
| 7-285828 | 10/1995 | Japan. |
| 9-067244 | 3/1997 | Japan. |
| WO 9307856 | 4/1993 | WIPO. |
| WO 9311736 | 6/1993 | WIPO. |
| WO 9501383 | 1/1995 | WIPO. |
| WO 9636310 | 11/1996 | WIPO. |

OTHER PUBLICATIONS

Derwent Abstract of EP–A–0 455 081.
Derwent Abstract of JP 03 184 910.

*Primary Examiner*—Thurman K. Page
*Assistant Examiner*—P. Kulkosky
*Attorney, Agent, or Firm*—Finnegan Henderson Farabow Garrett & Dunner, L.L.P.

[57] ABSTRACT

A method for coating keratinous substances including applying an agent for coating keratinous substances comprising:

(1) an aqueous/organic solution containing:
 (a) at least one non-crosslinked polymer capable of forming a deposit or a film on a keratinous substrate after drying and exhibiting a critical temperature Tc for solubility in water of the LCST or UCST type ranging from 0° to 100° C.; and
 (b) at least one total organic solvent for the polymer within the temperature range for use of the composition which is partially or completely miscible with water and more volatile than water; or (2) an aqueous solution or aqueous dispersion containing:
 (a) at least one non-crosslinked polymer capable of forming a deposit or a film on a keratinous substrate after drying and exhibiting a critical temperature Tc for solubility in water of the LCST or UCST type ranging from 0° to 100° C.; and
 (b) at least one surfactant and/or one hydrophilic polymer which are capable of establishing physical interactions with the non-crosslinked polymer; and cosmetic or dermatological compositions including these agents, in particular, hair form retention and/or styling products or make-up products of an aqueous nature.

58 Claims, No Drawings

COSMETIC OR DERMATOLOGICAL COMPOSITIONS CONTAINING POLYMERS EXHIBITING A CRITICAL TEMPERATURE OF THE LCST TYPE OR OF THE USCT TYPE OF USES THEREOF

The present invention relates to cosmetic or dermatological compositions containing non-crosslinked polymers capable of forming, after drying, a deposit or a film on a keratinous substrate, and exhibiting a critical temperature Tc for solubility in water of the LCST or UCST type, as well as to their various applications, in particular in the fields of hair and make-up products.

"Leave-in" cosmetic or dermatological products will be understood as meaning, throughout the description, any product whose application on keratinous substances to be treated is not followed by a rinsing with water.

"Rinse-out" cosmetic or dermatological products will be understood as meaning, throughout the description, any product whose application on keratinous substances to be treated is followed by a rinsing with water.

Keratinous substances will be understood as meaning, throughout the description, substances to be treated cosmetically or dermatologically chosen from the skin, scalp, hair, eyelashes, eyebrows, nails or mucous membranes.

Numerous leave-in cosmetic applications involve the transportation of a polymer from an organic, aqueous or aqueous/organic solution which leaves, after drying and evaporation of the solution, on the keratinous substance to be treated, a deposit or a film exhibiting mechanical characteristics specific to the use envisaged. This is the case, for example, with styling products, such as hair lacquers, generally containing alcohols, or alternatively make-up products, such as nail varnishes, generally containing solvents of the vinyl acetate type.

When the polymer is soluble in an organic solvent, it generally has a good affinity with the keratinous substance to be treated. During the drying and evaporation phase of the solvent, after application on the keratinous substrate, the polymer generally retains a residue of the solvent, which has a tendency, on the one hand, to substantially affect the desired mechanical properties of the film or deposit, by temporarily plasticizing it for a fairly long period of time and by substantially decreasing its stiffness and, on the other hand, to substantially prolong the drying time, which makes application difficult and is harmful to the comfort of the user. In the context of products for styling and/or for form retention of the hair, films or deposits which are difficult to disentangle are generally obtained under such conditions and, in the context of nail varnishes or nail care bases, films which are excessively soft, indeed sticky, to the touch and which change with time, are obtained.

When the polymer is dissolved in an aqueous or aqueous/organic solution, the film or the deposit obtained after drying and evaporation of the solution, in addition to the disadvantages stated above, will have a tendency to be very sensitive to ambient moisture and to show little resistance to water, which is a particular nuisance in styling products and make-up products where good water persistence is desired.

To overcome these various problems, provision has been made for the use, in place of film-forming polymers in organic, aqueous or aqueous/organic solutions, of aqueous dispersions of film-forming polymer particles of the latex or pseudolatex type. In the context of products for styling and/or for form retention of the hair, and more particularly hair lacquers, in order to obtain a film or a deposit on the hair exhibiting satisfactory mechanical and cosmetic characteristics, it is necessary to use the polymers at high concentrations on a dry basis (generally of the order of 15 to 20% by weight). Drying times are then obtained which are much too long. By increasing the solids content in the latex or pseudolatex, the drying time is substantially reduced but a "boarding" effect on the hair is obtained, due to an excessively high fixing power, which is not very desirable cosmetically, and significant difficulties of disentangling and of removing the shampoo appear.

One of the objectives of the present invention is to identify, for use in leave-in cosmetic products, new polymer solutions which make it possible, within substantially shorter drying times, to obtain a film or a deposit exhibiting satisfactory mechanical and cosmetic properties which do not change in the envisaged cosmetic application, while reducing as much as possible the amount of solvent trapped in the film or deposit after drying.

Numerous rinse-out cosmetic applications involve the use of a polymer in solution or in dispersion in an aqueous medium which has to provide a deposit after application on the keratinous substance to be treated and after rinsing with water. This is the case, for example, with styling or conditioning shampoos generally containing a high concentration of surfactants and a polymer capable of being deposited on the hair in order to introduce a form-retention effect or a conditioning effect which makes it possible to improve certain cosmetic properties, such as disentangling, feel, gloss or suppleness. This is also the case with skin hygiene products, such as bath or shower formulations, or make-up removal products. However, after application and rinsing with water, most of the polymer is generally removed and the deposit formed on the hair or the skin is too slight, perhaps nonexistent, to efficiently contribute the cosmetic properties desired.

Another objective of the present invention is thus to identify, for use in rinse-out cosmetic products, new polymer aqueous solutions or dispersions which make it possible to obtain, on the keratinous substance to be treated, after application and rinsing with water, an amount of polymer deposit which is sufficient to contribute the cosmetic properties desired according to the application envisaged.

Specific polymers with a solubility in water which is modified beyond a certain temperature are known in the state of the art. These are polymers exhibiting a critical temperature (or cloud point) defining their solubility region in water. This temperature is known as the "LCST" (Lower Critical Solution Temperature) when, above this temperature, the polymer loses its solubility in water and becomes soluble in water below this critical temperature. This temperature is known as the "UCST" (Upper Critical Solution Temperature) when, below this temperature, the polymer loses its solubility in water and becomes soluble in water above this critical temperature. These polymers are described in particular in the article by A. S. Hoffman, Macromol. Symp., 98, pp. 645–664 (1995), as well as in the work "Comprehensive Polymer Science, pp. 122–124, 1989, Pergamon Press," the disclosures of which are specifically incorporated by reference herein. According to the teaching of European Patent Applications EP-A-0,583,814 and EP-A-0,629,649, the disclosures of which are specifically incorporated by reference herein, some polymers having a critical temperature of the LCST type are used as temperature-reversible thickening additives in the manufacture of fluids or lubricants used in many industrial sectors.

The inventors have discovered, surprisingly, that some non-crosslinked polymers having a critical temperature Tc for solubility in water of the LCST or UCST type ranging from 0° C. to 100° C., in combination with an appropriate aqueous/organic solvent system, produced, after application on keratinous substances and drying of the solvent system, a film or a deposit exhibiting satisfactory mechanical and cosmetic properties for contributing the cosmetic properties desired according to the application envisaged; the drying times being substantially shorter than those of the film-forming polymer solutions conventionally used in leave-in cosmetic products and the levels of residual solvent trapped in the film or the deposit obtained after drying are substantially lower, perhaps nonexistent.

The inventors have also discovered that these same specific polymers, in combination with an appropriate aqueous medium containing surfactants and/or certain hydrophilic polymers capable of establishing physical interactions with the said polymers of the invention, made it possible to obtain, after application on keratinous substances and rinsing with water, an amount of polymer deposit sufficient to contribute the cosmetic properties desired according to the application envisaged.

A subject of the invention thus relates to the use, as an agent for coating keratinous substances, in and for the preparation of cosmetic or dermatological compositions, of an aqueous/organic solution containing:
- (a) at least one non-crosslinked polymer capable of forming a deposit or a film on a keratinous substrate after drying and exhibiting a critical temperature Tc for solubility in water of the LCST or UCST type ranging from 0° to 100° C.; and
- (b) at least one total organic solvent for the polymer within the temperature range for use of the composition which is partially or completely miscible with water and more volatile than water.

The invention also relates to cosmetic or dermatological compositions comprising, as an agent for coating keratinous substances, at least one aqueous/organic solution containing:
- (a) at least one non-crosslinked polymer capable of forming a deposit or a film on a keratinous substrate after drying and exhibiting a critical temperature Tc for solubility in water of the LCST or UCST type ranging from 0° to 100° C.; and
- (b) at least one total organic solvent for the polymer in the temperature range for use of the composition which is partially or completely miscible with water and more volatile than water. This type of composition is more particularly suited to leave-in applications.

Another subject of the invention relates to the use, as an agent for coating keratinous substances, in and for the preparation of cosmetic or dermatological compositions, of an aqueous solution or of an aqueous dispersion containing:
- (a) at least one non-crosslinked polymer capable of forming a deposit on a keratinous substrate after drying and exhibiting a critical temperature Tc for solubility in water of the LCST or UCST type ranging from 0° to 100° C.; and
- (b) at least one surfactant and/or at least one hydrophilic polymer not exhibiting a critical temperature Tc within the range indicated above which are capable of establishing physical interactions with the polymer.

The invention also relates to cosmetic or dermatological compositions containing, as an agent for coating keratinous substances, at least one aqueous solution or one aqueous dispersion containing:
- (a) at least one polymer capable of forming, after drying and evaporation, a deposit or a film on a keratinous substrate and exhibiting a critical temperature Tc for solubility in water of the LCST type or of the UCST type ranging from 0° to 100° C.; and
- (b) at least one surfactant and/or at least one hydrophilic polymer not exhibiting a critical temperature Tc within the range indicated above, which are capable of establishing physical interactions with the polymer. This type of composition is very particularly suited to rinse-out products.

Other subjects will become apparent in the light of the description and examples which follow.

The temperature for use of the compositions of the invention generally varies from 0 to 100° C., and more particularly corresponds to room temperature.

The critical temperature Tc for solubility in water preferably varies from 0° to 100° C., and more preferably varies from 10° to 80° C.

The polymers according to the invention, exhibiting a critical temperature Tc in the range indicated above, of the LCST type are preferably selected from:
- (i) non-crosslinked homopolymers or copolymers of monomers containing an amide group, for example poly(N-substituted acrylamide)s, such as poly(N-isopropylacrylamide) homopolymers, copolymers of N-isopropylacrylamide and of $C_1$–$C_{18}$ ester of (meth)acrylic acid (for example, butyl acrylate) or copolymers of N-isopropylacrylamide and of methacrylic acid; polymers or copolymers of vinylcaprolactam; or poly(alkyloxazoline)s;
- (ii) non-crosslinked homopolymers or copolymers of monomers containing at least one ether group, such as poly(ethylene oxide)s; ethylene oxide/propylene oxide diblock copolymers; poly(ethylene oxide)/poly(propylene oxide)/poly(ethylene oxide) triblock copolymers; or poly(vinyl methyl ether)s;
- (iii) non-crosslinked homopolymers or copolymers of monomers containing at least one alcohol group, such as poly(hydroxyalkyl acrylate)s; cellulose ethers, such as ethyl hydroxyethylcellulose, hydroxyethylcellulose, hydroxypropylcellulose or methylcellulose; poly(vinyl alcohol) and their derivatives; and
- (iv) poly(dimethylaminoethyl methacrylate)s.

The polymers according to the invention exhibiting a critical temperature for solubility in water of the LCST or UCST type are present in the compositions in accordance with the invention in concentrations preferably ranging from 0.1 to 50% by weight, and more preferably from 0.5 to 40% by weight, with respect to the total weight of the composition. The concentration of polymer will ultimately depend on the cosmetic or dermatological application envisaged.

The organic solvents used in the compositions of the invention are selected from all cosmetically acceptable organic solvents capable of completely dissolving the polymers of the invention in the temperature range of use. They must be partially or completely miscible with water and more volatile than water.

The organic solvents that may be used in accordance with the compositions of the invention are preferably selected from:
- $C_1$–$C_4$ lower alcohols, such as ethanol, isopropanol or n-propanol;
- ethers, such as dimethoxyethane;
- ketones, such as acetone or methyl ethyl ketone; and
- $C_1$–$C_3$ lower carboxylic acid esters, such as methyl acetate or ethyl acetate.

The organic solvents of the invention are present in the compositions in accordance with the invention in concentrations preferably ranging from 5 to 90% by weight, and more preferably from 10 to 70% by weight, with respect to the total weight of the water/organic solvent(s) mixture.

A specific form of the invention includes compositions containing at least one surfactant and/or at least one additional hydrophilic polymer (soluble or dispersible in water) not exhibiting a critical temperature of the LCST or UCST type within the range recommended by the invention which are capable of establishing physical interactions with the polymers of the invention. These physical interactions can be of the ionic, polar, dipolar, hydrophobic or hydrogen bond type.

Mention may be made, among the additional hydrophilic polymers capable of interacting with the polymers of the invention and which do not exhibit a critical temperature of the LCST or UCST type within the range recommended by the invention, of, for example:

poly(vinyl alcohol)s and their copolymers, in particular with vinyl acetate or ethylene;

polysaccharides or cellulose polymers, such as cellulose ethers which are soluble in water, carboxymethylcelluloses, cationic celluloses, hydroxypropylated guar gums, guar gums containing both hydroxypropyl groups and ionic groups, such as carboxymethyl or trimethylammonium chloride, xanthan gums, gellan, chitosan or hyaluronic acid;

natural proteins or synthetic polypeptides;

synthetic polymers of monomers containing amide groups, such as homopolymers or copolymers of vinylpyrrolidone; or copolymers based on monomers containing anionic groups, such as carboxyl, sulphonic or phosphonic groups, for example poly(acrylamidosulphonic acid)s and poly(vinylphosphonic acid) polymers.

These additional hydrophilic polymers are present in the compositions in accordance with the invention in concentrations preferably ranging from 5 to 50% by weight, and more preferably from 10 to 30% by weight, with respect to the total weight of all the polymers present in the composition.

The surfactant or surfactants used in combination with the polymers having a critical temperature of the LCST or UCST type within the range indicated above can be selected, without distinction, alone or as mixtures, from anionic, amphoteric, non-ionic, zwitterionic and cationic surfactants.

Thus, according to the invention, the surfactants can preferably represent from 4% to 30% by weight, more preferably from 10% to 25% by weight, and more preferably still from 12% to 20% by weight, of the total weight of the final composition.

The surfactants which are suitable for the implementation of the present invention are in particular as follows:

(i) Anionic Surfactant(s):

Their nature does not assume a really critical character within the context of the present invention.

Thus, by way of example of anionic surfactants that can be used, alone or as mixtures, in the context of the present invention, there may be mentioned in particular, the salts, in particular alkali metal, and especially sodium, salts, ammonium salts, amine salts, aminoalcohol salts and magnesium salts of the following compounds: alkyl sulphates; alkyl ether sulphates; alkylamido ether sulphates; alkylarylpolyether sulphates; monoglyceride sulphates; alkylsulphonates; alkyl phosphates; alkylamidesulphonates; alkylarylsulphonates; α-olefinsulphonates; paraffinsulphonates; alkyl sulphosuccinates; alkyl ether sulphosuccinates; alkylamidesulphosuccinates; alkyl sulphosuccinamates; alkyl sulphoacetates; alkyl ether phosphates; acylsarcosinates; acylisethionates; and N-acyltaurates; the alkyl or acyl radical of each of these different compounds preferably containing from 12 to 20 carbon atoms, and the aryl radical preferably denoting a phenyl or benzyl group. Among the anionic surfactants which are further usable, there may also be mentioned the salts of fatty acids such as the salts of oleic, ricinoleic, palmitic and stearic acids, the acids of copra oil or of hydrogenated copra oil, and acyllactylates in which the acyl radical contains 8 to 20 carbon atoms. It is also possible to use weakly anionic surfactants, like alkyl-D-galactosideuronic acids and salts thereof, as well as the polyoxyalkylenated ether carboxylic acids and salts thereof, in particular those containing from 2 to 50 ethylene oxide groups, and mixtures thereof. The anionic surfactants of the polyoxyalkylenated ether carboxylic salt or acid type are in particular those which correspond to the following formula (1):

$$R_1-(-OC_2H_4-)_n-OCH_2COOA \qquad (1)$$

in which:

$R_1$ denotes an alkyl or alkylaryl group and n is an integer or decimal number (mean value) which can vary from 2 to 24 and preferably from 3 to 10, the alkyl radical having from approximately 6 to approximately 20 carbon atoms and aryl preferably denoting phenyl, A denotes H, ammonium, Na, K, Li, Mg or a monoethanolamine or triethanolamine residue.

Use may also be made of mixtures of compounds of formula (1), in particular mixtures in which the $R_1$ groups are different.

Compounds of formula (1) are sold, for example, by the Company Chem Y under the names AKYPOS (NP40, NP70, OP40, OP80, RLM25, RLM38, RLMQ38 NV, RLM 45, RLM 45 NV, RLM 100, RLM 100 NV, RO20, RO90, RCS 60, RS 60, RS 100, RO 50) or by the Company Sandoz under the names SANDOPAN (DTC ACID, DTC).

(ii) Non-ionic Surfactant(s):

The non-ionic surface-active agents themselves are also compounds which are well known per se, in this respect, see in particular, the "Handbook of Surfactants" by M. R. Porter, published by Blackie & Son (Glasgow and London), 1991, pp. 116–178, and, in the context of the present invention, their nature does not assume any critical character. They can thus be selected from the nonlimiting list: alcohols, alphadiols, alkylphenols or polyethoxylated, polypropoxylated or polyglycerolated fatty acids which have a fatty chain containing, for example, 8 to 18 carbon atoms, it being possible for the number of ethylene oxide or propylene oxide groups to range especially from 2 to 50 and it being possible for the number of glycerol groups to range especially from 2 to 30. The copolymers of ethylene and propylene oxide and the condensates of ethylene and propylene oxide with fatty alcohols may also be mentioned; the polyethoxylated fatty amides preferably having from 2 to 30 mol of ethylene oxide, the polyglycerolated fatty amides on average containing 1 to 5 glycerol groups, and in particular 1.5 to 4; the polyethoxylated fatty amines preferably having 2 to 30 mol of 10 ethylene oxide; the oxyethylenated esters of sorbitan fatty acids having from 2 to 30 mol of ethylene oxide; the sucrose esters of fatty acids, the polyethylene glycol esters of fatty acids, the alkylpolyglycosides, the N-alkylglucamine derivatives, the amine oxides such as the oxides of $(C_{10}-C_{14})$alkylamines or the N-acylaminopropylmorpholine oxides. It will be noted that alkylpolyglycosides constitute non-ionic surfactants which work particularly well in accordance with the present invention.

(iii) Amphoteric or Zwitterionic Surfactant(s):

The amphoteric or zwitterionic surface-active agents, the nature of which does not assume any critical character in the context of the present invention, may preferably be derivatives of aliphatic secondary or tertiary amines in which the aliphatic radical is a linear or branched chain containing 8 to 18 carbon atoms and containing at least one water-solubilizing anionic group (for example carboxylate, sulphonate, sulphate, phosphate or phosphonate); ($C_8$–$C_{20}$) alkylbetaines, sulphobetaines, ($C_8$–$C_{20}$)alkylamido($C_1$–$C_6$) alkylbetaines or ($C_8$–$C_{20}$)alkylamido($C_1$–$C_6$) alkylsulphobetaines, may further be mentioned.

Among the amine derivatives, there may be mentioned products sold under the name MIRANOL, as described in United States Patents U.S. Pat. No. 2,528,378 and U.S. Pat. No. 2,781,354, the disclosures of which are specifically incorporated by reference herein, and classified in the CTFA dictionary, 3 rd edition, 1982 under the names Amphocarboxyglycinates and Amphocarboxypropionates, with respective structures:

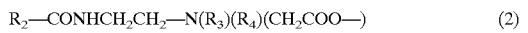

$$R_2\text{—CONHCH}_2\text{CH}_2\text{—N}(R_3)(R_4)(CH_2COO\text{—}) \quad (2)$$

in which: $R_2$ denotes an alkyl radical of an acid $R_2$—COOH present in hydrolysed copra oil, a heptyl, nonyl or undecyl radical, $R_3$ denotes a beta-hydroxyethyl group and $R_4$ a carboxymethyl group; and

$$R_2\text{—CONHCH}_2\text{CH}_2\text{—N(B)(C)} \quad (3)$$

in which:

B represents —$CH_2CH_2OX'$, C represents —$(CH_2)_z$—Y', wherein z denotes 1 or 2, X' denotes the —$CH_2CH_2$—COOH group or a hydrogen atom, Y' denotes —COOH or the radical —$CH_2$—CHOH—$SO_3H$, and $R_2$ denotes an alkyl radical of an acid $R_9$—COOH present in hydrolysed linseed oil or copra oil, an alkyl radical, in particular $C_7$, $C_9$, $C_{11}$ or $C_{13}$, a $C_{17}$ alkyl radical and its isoform, or an unsaturated $C_{17}$ radical.

By way of preferred example, there may be mentioned the cocoamphocarboxyglycinate sold under the trade name MIRANOL $C_2M$ concentrate by the Company Miranol.

(iv) Cationic Surfactants:

Among the cationic surfactants, the nature of which does not assume a critical character within the context of the present invention, there may be mentioned in particular: the salts of optionally polyoxyalkylenated primary, secondary or tertiary fatty amines; quaternary ammonium salts, such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature. It will be noted that the cationic surfactants, the use of which is not ruled out, do not constitute preferred surfactants for the implementation of the present invention.

In a known way, all the compositions of the invention can contain adjuvants usually found in the cosmetics and dermatological fields: oils, waxes or other standard fatty substances, or conventional gelling agents and/or thickeners; emulsifiers; moisturizing agents; emollients; sunscreens; hydrophilic or lipophilic active agents, such as ceramides; agents for combatting free radicals; bactericides; sequestering agents; agents for combating dandruff, antioxidants; preservatives; basifying or acidifying agents; fragrances; fillers; or colouring materials. The amounts of these various adjuvants are those conventionally used in the fields under consideration.

Of course, a person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in all the forms appropriate for a topical application, in particular in the form of solutions of the lotion or serum type; in the form of aqueous gels; or in the form of emulsions obtained by dispersion of a fatty phase in an aqueous phase (O/W) or vice versa (W/O), with a more or less thickened liquid consistency, such as milks or more or less smooth creams. These compositions are prepared according to the usual methods.

The compositions according to the invention can be used as hair products, in particular for washing, caring for, or conditioning or form retention of the hairstyle or shaping keratinous fibres, such as the hair.

The leave-in hair compositions according to the invention are preferably styling products, such as hair-setting lotions, blow-drying lotions or fixing and styling compositions, such as lacquers or sprays. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray or a foam for fixing or treating the hair.

The rinse-out hair compositions are more particularly styling and/or conditioning shampoos, or alternatively rinse-out conditioners.

The compositions of the invention can also be used as care and/or hygiene product, such as protection, treatment or care creams for the face, for the hands or for the body, protection or care body milks or lotions, gels or foams for caring for the skin and mucous membranes and for cleansing the skin.

The compositions of the invention can also be used as make-up removal products.

The compositions according to the invention can be make-up products and more particularly nail varnishes or nail care bases.

Another subject of the invention is a process for the non-therapeutic cosmetic treatment of the skin, scalp, hair, eyelashes, eyebrows, nails or mucous membranes, characterized in that a composition as defined above is applied to the keratinous substrate according to the usual technique for the use of this composition.

The examples which follow serve to illustrate the present invention without, however, having a limiting nature.

EXAMPLE 1

Synthesis of Homopoly(N-isopropylacrylamide)

A N-isopropylacrylamide monomer was purified by dissolving in acetone and recrystallizing from petroleum ether.

The following were introduced into a reactor equipped with a central stirrer, a thermometer and a nitrogen inlet pipe:

| | |
|---|---|
| N-Isopropylacrylamide | 50 g |
| Methyl ethyl ketone (solvent) | 125 g |
| t-Butyl 2-ethylhexanoate, sold under the name TRIGONOX by Akzo | 2 g |

Polymerization was carried out under nitrogen and with stirring for 18 hours at 79° C. The polymer was precipitated from ethyl ether and was then filtered off and washed with diethyl ether. The polymer was dried under vacuum at 40° C. for 24 hours.

The critical temperature Tc for solubility of the LCST type of this polymer was subsequently measured visually and by DSC using a device of the "ROBOTEC SYSTEM DSC 7 RS" type sold by the company Perkin-Elmer.

According to the visual method, a solution of the polymer in water was prepared at a given concentration and then the solution was placed in a flask. The latter was placed in a thermostatically-controlled bath. When the Tc to be determined was greater than 20° C., the temperature of the bath was gradually raised in steps of 0.5° C., with a stationary phase of 10 minutes at each temperature. When the Tc to be determined was lower than 20° C., the flask was placed in a thermostatically-controlled bath, the temperature of which was regulated by a cryostat, and the temperature was gradually lowered in steps of 0.5° C., with a stationary phase of 10 minutes at each temperature. The temperature at which cloudiness began was determined visually.

According to the DSC method, the value of the temperature Tc was determined with respect to the first rise in temperature of the sample with a rate of temperature rise of 0.1° C./minute. The value of the transition was calculated at the maximum of the peak.

The polymer obtained exhibited a critical temperature of the LCST type equal to approximately 31° C. in a 5% by weight solution in water.

EXAMPLE 2

Synthesis of a Copolymer of N-isopropylacrylamide and of Butyl Acrylate

The synthesis was carried out under the same conditions as those employed in Example 1, use being made of a mixture of monomers including:

| | |
|---|---|
| N-Isopropylacrylamide | 90% by weight |
| Butyl acrylate | 10% by weight |

The copolymer obtained exhibited a critical temperature of the LCST type equal to approximately 19° C. in a 5% by weight solution in water.

EXAMPLE 3

Synthesis of a Copolymer of N-isopropylacrylamide and of Acrylic Acid

The synthesis was carried out under the same conditions as those employed in Example 1, use being made of a mixture of monomers including:

| | |
|---|---|
| N-Isopropylacrylamide | 90% by weight |
| Acrylic acid | 10% by weight |

The copolymer obtained exhibited a critical temperature of the LCST type equal to approximately 30.7° C. in a 5% by weight solution in water.

EXAMPLE 4

Synthesis of a Copolymer of N-isopropylacrylamide and of Dimethylaminoethyl Methacrylate The synthesis was carried out under the same conditions as those employed in Example 1, use being made of a mixture of monomers including:

| | |
|---|---|
| N-Isopropylacrylamide | 90% by weight |
| Dimethylaminoethyl methacrylate | 10% by weight |

The copolymer obtained exhibited a critical temperature of the LCST type equal to approximately 29° C. in a 5% by weight solution in water.

EXAMPLE 5

Aqueous/alcoholic Hair Aerosol Lacquer for Fixing the Hair

An aerosol lacquer was prepared by dissolving 7 g of polymer according to Example 1 in a mixture including 27.9 g of ethanol and 18.6 g of water (ethanol/water mixture; 60/40% by weight). The clear solution obtained was introduced into an aerosol device containing 50 g of dimethyl ether propellent.

A hair lacquer was thus obtained which, after very rapid drying (with a time equivalent to that of an alcoholic lacquer), produced a deposit on the hair which contributed good fixing of sufficient stiffness without being sticky to the touch. The deposit readily disentangled on passing a comb or brush through the hair.

EXAMPLE 6

Aqueous/alcoholic Hair Aerosol Lacquer for Fixing the Hair

An aerosol lacquer was prepared by dissolving 7 g of polymer according to Example 2 in a mixture including 27.9 g of ethanol and 18.6 g of water (ethanol/water mixture; 60/40% by weight). The clear solution obtained was introduced into an aerosol device containing 50 g of dimethyl ether propellent.

A hair lacquer was also obtained which, after very rapid drying despite the large amount of water (with a time equivalent to that of an alcoholic lacquer), produced a deposit on the hair which contributed good fixing of sufficient stiffness without being sticky to the touch. The deposit readily disentangled on passing a comb or brush through the hair.

We claim:

1. A method for coating a keratinous substance, said method comprising:

coating said keratinous substance with a cosmetic or dermatological composition comprising an aqueous/organic solution containing:

(a) at least one non-crosslinked polymer capable of forming, after drying, a deposit or a film on said keratinous substance, said polymer exhibiting a critical temperature Tc for solubility in water of the LCST or UCST type ranging from 0° to 100° C.; and (b) at least one organic solvent which is partially or completely miscible with water and more volatile than water.

2. A method for coating keratinous substances, said method comprising:

coating said keratinous substance with a cosmetic or dermatological composition comprising an aqueous solution or an aqueous dispersion containing:

(a) at least one non-crosslinked polymer capable of forming, after is drying, a deposit or a film on said keratinous substances, said polymer exhibiting a critical temperature Tc for solubility in water of the LCST or UCST type ranging from 0° to 100° C.; and (b) at least one surfactant and/or at least one hydrophilic polymer, said at least one surfactant and said at least one hydrophilic polymer not exhibiting a critical temperature Tc of the LCST or UCST type ranging from 0° to 100° C., wherein said at least one surfactant and/or said at least one hydrophilic polymer is capable of establishing a physical interaction with said at least one non-crosslinked polymer.

3. A method according to claim 2, wherein said physical interaction is selected from ionic, polar, dipolar, hydrophobic and hydrogen bond interactions.

4. A method according to claim 1, wherein said coating occurs at a temperature ranging from 0° C. to 100° C.

5. A method according to claim 2, wherein said coating occurs at a temperature ranging from 0° C. to 100° C.

6. A method according to claim 1, wherein said critical temperature Tc for solubility in water varies from 10° to 80° C.

7. A method according to claim 2, wherein said critical temperature Tc for solubility in water varies from 10° to 80° C.

8. A method according to claim 1, wherein said at least one non-crosslinked polymer exhibiting a critical temperature Tc of the LCST type is selected from:

(i) non-crosslinked homopolymers and copolymers of monomers containing an amide group;

(ii) non-crosslinked homopolymers and copolymers of monomers containing at least one ether group;

(iii) non-crosslinked homopolymers and copolymers of monomers containing at least one alcohol group; and (iv) poly(dimethylaminoethyl methacrylate)s.

9. A method according to claim 2, wherein said at least one non-crosslinked polymer exhibiting a critical temperature Tc of the LCST type is selected from:

(i) non-crosslinked homopolymers and copolymers of monomers containing an amide group;

(ii) non-crosslinked homopolymers and copolymers of monomers containing at least one ether group;

(iii) non-crosslinked homopolymers and copolymers of monomers containing at least one alcohol group; and (iv) poly(dimethylaminoethyl methacrylate)s.

10. A method according to claim 1, wherein said at least one organic solvent is selected from:

$C_1$–$C_4$ lower alcohols;

ethers;

ketones; and $C_1$–$C_3$ lower carboxylic acid esters.

11. A method according to claim 10, wherein said $C_1$–$C_4$ lower alcohols are selected from ethanol, isopropanol and n-propanol.

12. A method according to claim 10, wherein said at least one organic solvent is the ether dimethoxyethane.

13. A method according to claim 10, wherein said ketones are selected from acetone and methyl ethyl ketone.

14. A method according to claim 10, wherein said $C_1$–C3 lower carboxylic acid esters are selected from methyl acetate and ethyl acetate.

15. A method according to claim 1, wherein said aqueous/organic solution further contains at least one surfactant and/or at least one hydrophilic polymer, said at least one surfactant and said at least one hydrophilic polymer not exhibiting a critical temperature Tc of the LCST or UCST type ranging from 0° to 100° C., wherein said at least one surfactant and/or at least one hydrophilic polymer is capable of establishing a physical interaction with said at least one non-crosslinked polymer, and wherein said at least one hydrophilic polymer is soluble or dispersible in water.

16. A method according to claim 15, wherein said physical interaction is selected from ionic, polar, dipolar, hydrophobic and hydrogen bond interactions.

17. A method according to claim 15, wherein said at least one hydrophilic polymer is selected from:

poly(vinyl alcohol)s and their copolymers;

polysaccharides and cellulose polymers;

natural proteins and synthetic polypeptides;

synthetic polymers of monomers containing amide groups; and copolymers based on monomers containing anionic groups.

18. A method according to claim 17, wherein said anionic groups of said monomers are selected from carboxyl, sulphonic and phosphonic groups.

19. A cosmetic or dermatological composition comprising, as an agent for coating a keratinous substance, at least one aqueous/organic solution containing:

(a) at least one non-crosslinked polymer capable of forming after drying, a deposit or a film on said keratinous substances, said polymer exhibiting a critical temperature Tc for solubility in water of the LCST or UCST type ranging from 0° to 100° C.; and (b) at least one organic solvent which is partially or completely miscible with water and more volatile than water.

20. A cosmetic or dermatological composition comprising, as an agent for coating a keratinous substance, at least one aqueous solution or aqueous dispersion containing:

(a) at least one non-crosslinked polymer capable of forming, after drying, a deposit or a film on said keratinous substances, said polymer exhibiting a critical temperature Tc for solubility in water of the LCST or UCST type ranging from 0° to 100° C.; and (b) at least one surfactant and/or at least one hydrophilic polymer, said at least one surfactant and said at least one hydrophilic polymer not exhibiting a critical temperature Tc of the LCST or UCST type ranging from 0° to 100° C.

21. A cosmetic or dermatological composition comprising, as an agent for coating keratinous substances, at least one aqueous/organic solution according to claim 15.

22. A cosmetic or dermatological composition according to claim 21, wherein said at least one hydrophilic polymer is present in a concentration ranging from 5 to 50% by weight relative to the total weight of all polymers present in said composition.

23. A cosmetic or dermatological composition according to claim 22, wherein said at least one hydrophilic polymer is present in a concentration ranging from 10 to 30% by weight relative to the total weight of all polymers present in said composition.

24. A cosmetic or dermatological composition according to claim 21, wherein said at least one surfactant is selected from anionic, amphoteric, non-ionic, zwitterionic and cationic surfactants.

25. A cosmetic or dermatological composition according to claim 21, wherein at least one surfactant is present in a concentration ranging from 4 to 30% by weight relative to the total weight of said composition.

26. A cosmetic or dermatological composition according to claim 25, wherein at least one surfactant is present in a concentration ranging from 10 to 25% by weight relative to the total weight of said composition.

27. A cosmetic or dermatological composition according to claim 26, wherein at least one surfactant is present in a concentration ranging from 12 to 20% by weight relative to the total weight of said composition.

28. A cosmetic or dermatological composition according to claim 19, wherein said at least one organic solvent is present in a concentration ranging from 5 to 90% by weight relative to the total weight of said aqueous/organic solution.

29. A cosmetic or dermatological composition according to claim 28, wherein said at least one total organic solvent is present in a concentration ranging from 10 to 70% by weight relative to the total weight of said aqueous/organic solution.

30. A cosmetic or dermatological composition according to claim 19, wherein said at least one non-crosslinked polymer is present in a concentration ranging from 0.1 to 50% by weight relative to the total weight of said composition.

31. A cosmetic or dermatological composition according to claim 30, wherein said at least one non-crosslinked polymer is present in a concentration ranging from 0.5 to 40% by weight relative to the total weight of said composition.

32. A cosmetic or dermatological composition according to claim 19, wherein said composition is a hair product for washing, caring for, conditioning or shaping keratinous fibres or form retention of the hairstyle.

33. A cosmetic or dermatological composition according to claim 20, wherein said composition is a hair product for washing, caring for, conditioning or shaping keratinous fibres or form retention of the hairstyle.

34. A cosmetic or dermatological composition according to claim 21, wherein said composition is a hair product for washing, caring for, conditioning or shaping keratinous fibres, or form retention of the hairstyle.

35. A cosmetic or dermatological composition according to claim 32, wherein said composition is a leave-in styling product.

36. A cosmetic or dermatological composition according to claim 33, wherein said composition is a rinse-out hair product.

37. A cosmetic or dermatological composition according to claim 34, wherein said composition is a rinse-out hair product.

38. A cosmetic or dermatological composition according to claim 36, wherein said composition is a shampoo or a conditioner.

39. A cosmetic or dermatological composition according to claim 37, wherein said composition is a shampoo or a conditioner.

40. A cosmetic or dermatological composition according to claim 19, wherein said composition is a care and/or hygiene product.

41. A cosmetic or dermatological composition according to claim 20, wherein said composition is a care and/or hygiene product.

42. A cosmetic or dermatological composition according to claim 21, wherein said composition is a care and/or hygiene product.

43. A cosmetic or dermatological composition according to claim 19, wherein said composition is a make-up removal product.

44. A cosmetic or dermatological composition according to claim 20, wherein said composition is a make-up removal product.

45. A cosmetic or dermatological composition according to claim 21, wherein said composition is a make-up removal product.

46. A cosmetic or dermatological composition according to claim 19, wherein said composition is a make-up product.

47. A cosmetic or dermatological composition according to claim 20, wherein said composition is a make-up product.

48. A cosmetic or dermatological composition according to claim 21, wherein said composition is a make-up product.

49. A cosmetic or dermatological composition according to claim 46, wherein said make-up product is a nail varnish or nail care base.

50. A cosmetic or dermatological composition according to claim 47, wherein said make-up product is a nail varnish or nail care base.

51. A cosmetic or dermatological composition according to claim 48, wherein said make-up product is a nail varnish or nail care base.

52. A method for the non-therapeutic cosmetic treatment of the skin, scalp, hair, eyelashes, eyebrows, nails or mucous membranes, said method comprising applying an effective amount of a composition according to claim 19 to a keratinous substrate.

53. A method for the non-therapeutic cosmetic treatment of the skin, scalp, hair, eyelashes, eyebrows, nails or mucous membranes, said method comprising applying an effective amount of a composition according to claim 20 to a keratinous substrate.

54. A method for the non-therapeutic cosmetic treatment of the skin, scalp, hair, eyelashes, eyebrows, nails or mucous membranes, said method comprising applying an effective amount of a composition according to claim 21 to a keratinous substrate.

55. A method according to claim 4, wherein said coating occurs at room temperature.

56. A method according to claim 5, wherein said coating occurs at room temperature.

57. A method according to claim 2, wherein said at least one hydrophilic polymer is selected from:

poly(vinyl alcohol)s and their copolymers;

polysaccharides and cellulose polymers;

natural proteins and synthetic polypeptides;

synthetic polymers of monomers containing amide groups; and copolymers based on monomers containing anionic groups.

58. A method according to claim 57, wherein said anionic groups of said monomers are selected from carboxyl, sulphonic and phosphonic groups.

* * * * *

UNITED STATES PATENT AND TRADEMARK OFFICE
CERTIFICATE OF CORRECTION

PATENT NO. : 6,159,457
DATED : December 12, 2000
INVENTOR(S) : Nathalie Mougin

It is certified that error appears in the above-identified patent and that said Letters Patent is hereby corrected as shown below:

Title page,
Item [54], in the Title,
Line 4, "USCT" should read -- UCST --;
Line 5, "OF USES" should read -- AND USES --.

Claim 2, column 11,
Line 14, between "after" and "drying", delete "is".

Claim 14, column 12,
Line 5, "$C_1$-$C_3$" should read -- $C_1$-$C_3$ --

Signed and Sealed this

Twenty fifth Day of September, 2001

Attest:

NICHOLAS P. GODICI
Attesting Officer
Acting Director of the United States Patent and Trademark Office